(12) United States Patent
Muller et al.

(10) Patent No.: US 10,335,295 B2
(45) Date of Patent: Jul. 2, 2019

(54) LINER FOR A PROSTHESIS CONFIGURED TO EVACUATE A VOLUME BETWEEN THE LINER AND A SOCKET USING A VALVE AND PUMP CHAMBER EACH POSITIONED WITHIN THE LINER

(71) Applicant: OTTO BOCK HEALTHCARE GMBH, Duderstadt (DE)

(72) Inventors: Andre Muller, Duderstadt (DE); Dominik Schmidt, Furtwangen (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 220 days.

(21) Appl. No.: 15/323,618

(22) PCT Filed: Jul. 21, 2015

(86) PCT No.: PCT/EP2015/001501
§ 371 (c)(1),
(2) Date: Jan. 3, 2017

(87) PCT Pub. No.: WO2016/012094
PCT Pub. Date: Jan. 28, 2016

(65) Prior Publication Data
US 2017/0143519 A1    May 25, 2017

(30) Foreign Application Priority Data

Jul. 22, 2014    (DE) .......................... 10 2014 010 683

(51) Int. Cl.
*A61F 2/78*    (2006.01)
*A61F 2/80*    (2006.01)

(52) U.S. Cl.
CPC .............. *A61F 2/7812* (2013.01); *A61F 2/80* (2013.01); *A61F 2002/7818* (2013.01)

(58) Field of Classification Search
CPC ............. A61F 2/78; A61F 2/7812; A61F 2/80
See application file for complete search history.

(56) References Cited

U.S. PATENT DOCUMENTS

| 5,507,836 A | 4/1996 | Pohlig |
| 5,728,170 A | 3/1998 | Becker et al. |
| 5,980,577 A | 11/1999 | Radis et al. |
| 6,361,568 B1 | 3/2002 | Hoerner |
| 6,544,292 B1 | 4/2003 | Laghi |

(Continued)

FOREIGN PATENT DOCUMENTS

| CN | 1078133 A | 11/1993 |
| CN | 1147370 A | 4/1997 |

(Continued)

OTHER PUBLICATIONS

PCT International Search Report for PCT International Patent Application No. PCT/EP2015/001501, dated Nov. 27, 2015.

*Primary Examiner* — Marcia L Watkins
(74) *Attorney, Agent, or Firm* — Holland & Hart, LLP

(57) ABSTRACT

A liner for a prosthesis includes an inner face and an outer face, at least one flow channel with at least one inlet opening and at least one outlet opening extending between the inner face and the outer face, and a one-way valve arranged in the course of the at least one flow channel in such a manner that a fluid can flow through it only from the at least one inlet opening towards the at least one outlet opening.

20 Claims, 14 Drawing Sheets

(56) References Cited

U.S. PATENT DOCUMENTS

| | | |
|---|---|---|
| 7,744,653 B2 | 6/2010 | Rush et al. |
| 8,197,555 B2 | 6/2012 | Laghi |
| 8,394,150 B2 | 3/2013 | Laghi |
| 8,480,759 B2 | 7/2013 | Pacanowsky et al. |
| 8,568,489 B2 | 10/2013 | Finlinson et al. |
| 8,906,113 B2 | 12/2014 | Mosler et al. |
| 9,155,636 B1 * | 10/2015 | Fikes ............... A61F 2/7812 |
| 9,925,072 B2 * | 3/2018 | Jonsson ............... A61F 2/80 |
| 2001/0016781 A1 | 8/2001 | Caspers |
| 2007/0032883 A1 | 2/2007 | Mantelmacher |
| 2007/0055383 A1 | 3/2007 | King |
| 2008/0086218 A1 | 4/2008 | Egilsson |
| 2008/0221706 A1 | 9/2008 | Scussel et al. |
| 2010/0023134 A1 | 1/2010 | Laghi |
| 2010/0070051 A1 | 3/2010 | Carstens |
| 2010/0185300 A1 | 7/2010 | Mackenzie |
| 2010/0249950 A1 | 9/2010 | Bielefeld |
| 2011/0071648 A1 | 3/2011 | McKinney |
| 2012/0123559 A1 | 5/2012 | Mosler et al. |
| 2012/0191217 A1 | 7/2012 | Mackenzie |
| 2012/0191218 A1 | 7/2012 | McCarthy |

FOREIGN PATENT DOCUMENTS

| | | |
|---|---|---|
| CN | 1946358 A | 4/2007 |
| CN | 101815870 A | 8/2010 |
| CN | 102427778 A | 4/2012 |
| CN | 103142334 A | 6/2013 |
| DE | 10237269 A1 | 10/2003 |
| DE | 102006054891 A1 | 6/2008 |
| EP | 1771659 A1 | 4/2007 |
| WO | 2007030609 A2 | 3/2007 |
| WO | 2009062489 A1 | 5/2009 |
| WO | 2010085336 A1 | 7/2010 |

* cited by examiner

LINER FOR A PROSTHESIS CONFIGURED TO EVACUATE A VOLUME BETWEEN THE LINER AND A SOCKET USING A VALVE AND PUMP CHAMBER EACH POSITIONED WITHIN THE LINER

TECHNICAL FIELD

The invention relates to a liner for a prosthesis, having an inner face and an outer face.

BACKGROUND

Such liners are pulled on over an amputation stump of the patient before said amputation stump is inserted into a rigid prosthesis socket. The prior art discloses various possible ways of securing the prosthesis socket, and therefore the prosthesis itself, on the amputation stump of the patient or on the liner which is worn over the amputation stump. A widely used method is one in which a volume is defined between the liner and the prosthesis socket and is closed off to be as airtight as possible, and an underpressure is built up within this volume and ensures that the prosthesis socket is sucked firmly onto the liner. Such a liner is known from WO 2009/062489 A1, for example. The inner face in this case bears on the amputation stump, while the outer face is in contact with a prosthesis socket, for example. The adherence to the amputation stump and to the prosthesis socket is improved by the liner being designed with an inner liner and with an outer liner. In particular, the proximal portion of the outer liner can be turned back over the proximal edge of the prosthesis socket.

Since leakages and slight seepage can always cause more air to flow into the volume that has thus been evacuated, it is important to ensure that the underpressure in this volume between liner and prosthesis socket is constantly maintained. In addition, for different modes of movement and forms of actuation of the amputation stump, it is expedient to generate and maintain different degrees of underpressure in the volume. For example, when walking using a below-knee prosthesis, it is necessary to generate a much stronger underpressure in the volume than is needed when the person wearing the prosthesis is seated, for example.

The prior art discloses a number of ways of maintaining the underpressure. Initially, the volume was evacuated, for example, by an electrically operated pump. However, this has a number of disadvantages. On the one hand, this means that the person wearing the prosthesis has to carry around the additional weight and volume of the pump and, on the other hand, the pump has to be provided with a constant supply of power, for example by batteries. In addition, the pump causes an annoying noise to develop, which detracts from the overall wearing comfort of the prosthesis.

For this reason, the separate, electrically operated pump was replaced in many designs by a mechanical pump in which the movement of the liner or of the amputation stump located in the liner is used to evacuate the volume between the liner and the prosthesis socket. Such designs are known, for example, from U.S. Pat. No. 8,197,555 B2 and US 2012/0191217. Both documents describe prostheses in which, in the distal area of the liner, a volume is present between the liner and the prosthesis socket, which volume is compressed in the loaded state, for example when standing. Air located in the volume is in this way forced through a one-way valve located in the prosthesis socket. In this way, the pressure in the interior of the volume is reduced and, consequently, the underpressure is maintained.

DE 10 2006 054 891 A1 discloses a cup-shaped prosthesis socket in which, in the posterior area, a flexible chamber formed by films is arranged in the interior of the prosthesis socket. This chamber too is compressed during walking movements, such that air contained in the chamber is forced out of the prosthesis socket via a dedicated outlet line, which is routed through the prosthesis socket, and via a one-way valve arranged on said outlet line. However, in contrast to the aforementioned embodiments, the pump chamber here is not arranged in the distal area of the amputation stump.

The function of such a pump, which uses the movement of the amputation stump to evacuate a volume, is described in EP 1 771 659 B1, for example. The interior of the pump chamber accommodates, for example, an elastically deformable material that applies the restoring force and thus ensures that the pump chamber deploys again in the unloaded state and receives air from the volume to be evacuated.

U.S. Pat. No. 8,357,206 B2 and US 2012/0191218 A1 each disclose a liner which is provided with a distributing or conducting layer on the outer face of the liner. This layer consists of a porous and gas-conducting material and in this way forms a pump chamber distributed across almost the entire amputation stump. Alternatively, a separate external pump can also be attached which sucks air and optionally moisture out of the distributing or conducting layer. In US 2012/0191218 A1, the liner in the distal area of the amputation stump is additionally porous or provided with a multiplicity of holes or passages in order thereby to remove liquid from the amputation stump.

However, in these embodiments too, an outlet valve and an outlet channel are needed, which are routed through the prosthesis socket in order to convey the air out of the volume that is to be evacuated between liner and prosthesis socket.

The one-way valves and outlet lines or outlet channels, which are needed to carry away the air removed from the volume by the pump, are generally arranged in the distal area of the prosthesis socket, the overall height of which is thereby increased and its construction thereby complicated. Since the prosthesis socket is adapted individually to the person wearing the prosthesis, it is desirable that the orthopedic technician performing this adaptation is able to make available a prosthesis socket that otherwise has the simplest possible configuration. Particularly in the case of amputations a short distance above the knee for example, it is necessary that the prosthetic knee adjoins the distal end of the prosthesis socket directly, and therefore the space available for an elaborate valve arrangement is inadequate in these cases.

SUMMARY

The object of the invention is therefore to propose a liner for a prosthesis, which liner is able to overcome the disadvantages of the prior art.

The invention achieves said object by making available a liner for a prosthesis, which liner has an inner face and an outer face and is characterized in that at least one flow channel with at least one inlet opening and at least one outlet opening extends between the inner face and the outer face, wherein a one-way valve is arranged in the course of the at least one flow channel in such a manner that medium can flow through it only from the at least one inlet opening to the at least one outlet opening. In this way, for example, a volume between the distal end of the liner and the prosthesis socket of the prosthesis can be easily evacuated by using the movement of the amputation stump, without one-way valves and flow channels having to be arranged in the distal area of the prosthesis socket. Moreover, a passage through the prosthesis socket is no longer necessary, such that the complicated seal for maintaining the vacuum in the area between the liner and the prosthesis socket is in particular no longer necessary. In this way, the design of the prosthesis socket is simplified, and the manufacturing costs thus also decrease.

Advantageously, between the inner face and the outer face, at least one pump chamber is fluidically connected to the at least one flow channel.

In this way, everything that is needed to evacuate the volume between the liner according to the present invention and a prosthesis socket worn over said liner can be arranged in the liner itself between the inner face and the outer face. Therefore, no add-ons or devices are needed that would have to be integrated or installed in the prosthesis socket.

The inlet opening of the flow channel represents a connection of the pump chamber to the volume that is to be evacuated. Preferably, the at least one pump chamber forms a distal end of the at least one flow channel, such that the inlet opening preferably opens directly into the pump chamber. In the loaded state of the liner, for example when standing with an upper leg prosthesis, the pump chamber is compressed. If the person wearing the prosthesis now performs a gait cycle, the distal area of the liner lifts away from a distal area of the socket wall in the swing phase. In this case, air located in the volume that is to be evacuated flows through the inlet opening of the flow channel into the pump chamber between inner face and outer face of the liner. In the subsequent stance phase, the inlet opening is closed off in an airtight manner by the socket wall of the prosthesis socket against which it is now pressed, such that the air located in the pump chamber cannot escape through the inlet opening. However, an area between the liner and the prosthesis socket can also be used as pump chamber.

Upon compression of the pump chamber, the air located in the pump chamber passes through the flow channel and the outlet opening which, like the pump chamber, is arranged between the inner face and the outer face of the liner. At the end of the flow channel opposite the pump chamber, which end is advantageously located at the proximal edge of the liner, the air is able to leave the liner. If the person wearing the prosthesis now performs further gait cycles, the air between the socket and the liner is evacuated with each step from the volume lying therebetween. An active vacuum is generated, hence the desired holding force between the amputation stump and the prosthesis socket. The amount of the air drawn off from the volume becomes less with each step, until an underpressure level has been established at which a release of the liner, pulled on over the amputation stump, from the inner wall of the socket of the prosthesis socket is prevented. In this way, there is no pumping or milking effect of the kind known from the prior art. This too can be achieved without or without a pump chamber integrated in the liner.

The liner according to the invention can be easily rolled on over the amputation stump by the prosthesis wearer. The prosthesis wearer then places the stump into the prosthesis socket. By virtue of the already described function of the liner according to the invention, it is not necessary, for example, to first of all use a separate external pump to set up a pre-vacuum or an initial underpressure in the volume between the liner and the prosthesis socket.

According to the invention, the at least one flow channel is connected to a one-way valve that prevents air from flowing in through the at least one outlet opening of the flow channel. The efficiency is further increased in this way since, particularly during the expansion of the area between the liner and the prosthesis socket or the pump chamber, when air from the volume to be evacuated is intended to pass through the inlet opening into the pump chamber or the flow channel, it is possible to prevent air from additionally flowing through the outlet opening into the flow channel.

It has proven particularly advantageous if the one-way valve is likewise arranged between the inner face and the outer face. In this configuration too, everything needed to evacuate the volume between the prosthesis socket and the liner is arranged between the inner face and the outer face, and it is therefore not necessary to provide separate additional components on the prosthesis socket.

Advantageously, the liner has, at least in sections, an inner liner and an outer liner. These are arranged on each other over part or all of their surface area and preferably together form the liner. The inner face of the liner is formed by the inner face of the inner liner, while the outer face of the liner is formed by the outer face of the outer liner. It has proven particularly advantageous if the flow channel and if appropriate also the pump chamber is arranged between the inner liner and the outer liner. The liner can in this way be produced in a particularly simple manner.

Preferably, the inner liner and/or the outer liner are made of polyurethane or silicone. It has proven particularly advantageous if the inner liner is made of polyurethane, while the outer liner is made of silicone.

In an advantageous embodiment of the present invention, the one-way valve is designed as a flutter valve. A flutter valve is a one-way valve that opens and also automatically closes again without any external drive. The opening and closing take place exclusively on account of pressure differences on the two sides of the valve. Such valves can be made very compact and small, require little maintenance and are not susceptible to defects. Moreover, this type of valve is particularly suitable in a liner that is constantly subject to elastic deformations.

Preferably, the one-way valve is formed from two liner layers, in particular from the inner liner and the outer liner. This can be done, for example, if the inner liner and outer liner, in the area intended to form the one-way valve, are not adhesively bonded or otherwise permanently connected to each other, such that a possible flow path forms here through which air is able to pass. In the loaded state of the prosthesis for which the liner is used, the air pressure at the distal end of the valve formed by the two liner layers is higher than at the proximal end, such that the air is forced through the one-way valve. In the unloading phase, however, air is not able to flow in reverse though the one-way valve thus formed, since the inner liner and the outer liner are pressed onto each other by the prevailing ambient pressure and, if appropriate, by pressure exerted from the prosthesis socket. This effect can be strengthened by underpressure that is present, for example, in the pump chamber or that is generated in the unloading phase.

However, it is not necessary to configure the one-way valve from the inner liner and the outer liner. As an alternative to this, for example, an additional liner layer that performs the desired function can be present only in the area in which the valve is provided.

In another possible embodiment, the one-way valve is formed by a single separate liner layer that is made of an air-permeable material and that thus forms the flow path through the one-way valve. This material can be used as an additional liner layer between layers that are present anyway and can thus be arranged, for example, between inner liner and outer liner. However, it is also possible to cast this material into a liner material of what is otherwise a one-piece liner for example. In this case too, in the loaded state of the prosthesis, air is forced through the material that acts as valve by the high air pressure prevailing in the pump chamber, while the prevailing ambient pressure and if appropriate the pressure applied by the prosthesis socket ensure that a back-flow of air in the opposite direction is prevented.

Advantageously, a valve beak of the flutter valve is composed of several film elements, in particular two film elements. In the expansion phase of the pump chamber, in which air from the volume to be evacuated flows through the inlet opening into the flow channel, the air pressure on the side of the one-way valve directed toward the inlet opening is lower than on the side directed away from the inlet opening, such that the valve is closed. The film elements forming the valve beak then bear on each other and are pressed together by the higher air pressure prevailing on the outer face, which is directed away from the inlet opening. Admission of air is not possible in this state.

As an alternative to this, the valve beak of the flutter valve can also be formed from just a single film element and, for example, the liner material. In this way, the number of components required is smaller, and therefore the design is simplified and the manufacturing costs reduced.

It is moreover possible to provide a further one-way valve on or in the inlet opening if the latter, for example, leads to the interior between the liner and the prosthesis socket. It is thereby possible to improve the pump action. In this way, the inlet opening is completely sealed off even in the event that this is not done by the prosthesis socket itself. In this case too, air can therefore be prevented from flowing back into the pump volume. This is advantageous, for example, in cases where the patient uses a stump stocking that can be worn over the liner. In this way, the pump performance is also not impaired in this case.

In the compression phase by contrast, in which the pump chamber or an area between liner and prosthesis socket is compressed on account of the external loads, the air pressure on the side of the one-way valve directed toward the inlet opening is higher than on the side directed toward the outlet opening, such that the one-way valve opens. The film elements forming the valve beak are forced apart, and the air is able to escape from the pump chamber through the one-way valve.

In a particularly simple embodiment of the present invention, the at least one inlet opening is a hole in the outer liner. Since the flow channel and if appropriate the pump chamber are in this case located, for example, between the inner liner and the outer liner, a hole in the outer liner produces a connection between the flow channel and if present the pump chamber and the volume outside the liner, which is consequently located between the liner and the prosthesis socket when the prosthesis is fitted in place. It has also proven advantageous if, in the case of a pump chamber being located in the liner, a corresponding one-way valve is also arranged at the at least one inlet opening, which one-way valve on the one hand allows air to flow into the pump chamber through the inlet opening but on the other hand prevents a situation where, in the phase in which the pump chamber is compressed, air leaves the pump chamber through the inlet opening. An additional one-way valve of this kind is particularly useful if it is not ensured, or not reliably ensured, that the at least one inlet opening is safely closed off in an airtight manner by the inner wall of the socket in the phase in which the pump chamber is compressed.

Preferably, the at least one pump chamber has a peripheral wall made of an elastically deformable material. This has the effect that, after the compression of the pump chamber by the action of an external force, the material applies an opposing or restoring force which, after cessation of the external force, ensures that the pump chamber expands again and thus sucks in air. The peripheral wall of the pump chamber is advantageously formed from the inner liner and the outer liner. This results in a particularly simple configuration of the pump chamber.

In addition or as an alternative to this, an elastically deformable material, in particular an open-pore material, is located in the pump chamber. This also ensures that a restoring force is exerted on the pump chamber and expands the pump chamber to its original size as soon as a force acting from outside and compressing the pump chamber ceases. The elastically deformable material can be arranged in strips or partition walls such that, between the individual elements of the elastically deformable material, sufficient space remains to take up air. However, the elastically deformable material can also be open-pored or porous and can thus itself take up air. A material of this kind can be, for example, an open-pore foam or a 3D matrix, for example in the form of a 3D knit. In this case, the entire pump chamber can be filled with the elastically deformable material. The applied restoring force is thereby maximized and the pump effect optimized.

Advantageously, the inner liner and the outer liner are arranged on each other in a proximal area of the liner in such a manner that the outer liner can be turned back separately from the inner liner. Inner liner and outer liner can be secured on each other and connected to each other in a wide variety of ways. For example, they can be arranged on each other in two separate dipping steps in which a blank or preform is dipped into a bath of liquid liner material. As an alternative to this, it is also possible for the inner liner and outer liner first to be produced separately and then to be secured on each other, for example, by an adhesively bonded connection. In the described advantageous embodiment, the inner liner and the outer liner are not connected to each other in the proximal area of the liner, such that the outer liner can be turned back separately from the inner liner. This has a number of advantages.

When a prosthesis socket is pulled over such a liner, the outer liner can be turned back separately from the inner liner over the proximal edge of the prosthesis socket. On the one hand, an airtight connection is thus obtained, such that the volume between the liner and the prosthesis socket is sealed off. On the other hand, it is in this way possible for the one-way valve lying between the inner liner and the outer liner, or for the outlet opening of the flow channel, to be freed in such a way that air can escape from the liner at this point. If the region in which the inner liner and the outer liner are not secured on each other in the proximal area of the liner is sufficiently dimensioned, it is thereby possible to use one liner for very different stump lengths of the amputation stumps.

The present invention thus proposes a liner which comprises a flow channel and a locking system as an integral constituent of the liner. The evacuation of the volume between the liner and the prosthesis socket and the resulting build-up of the holding force are achieved by the relative movement of the liner with respect to the prosthesis socket, for example when walking. The air evacuated in this way from the volume can be expelled at the partition edge of the two liner layers in the proximal area of the liner. In this way, the volume between the liner and the prosthesis socket can be evacuated without release valves, nonreturn valves or other devices having to be present in the socket.

In a preferred embodiment, the inlet opening is located distally and/or the outlet opening is located proximally on the liner. This also simplifies the design and at the same time has the effect that the required holding force can be applied in a reliable and reproducible manner.

Preferably, the liner is provided on its outer face with a textile, a fiber, a woven fabric or a surface structure. It is thus ensured that the applied underpressure acts within the entire space between the liner and the prosthesis socket and is able to "distribute" itself therein. This avoids a situation where the liner bears fully on the socket in sections and thus possibly prevents propagation of the underpressure.

Advantageously, one or more sealing lips are present on the outer face of the liner. These are preferably formed integrally on the liner in the radial direction or adhesively bonded or pushed on or otherwise secured on the liner. The sealing lips protrude radially above the outer circumference of the liner and, in the fitted state, ensure a sealed closure with respect to the inner face of a prosthesis socket. The sealing lips can be differently shaped and can be present in different numbers. It is often sufficient to provide one radially encircling sealing lip, whereas in other embodiments two or more sealing lips have to be present. The actual number, shape and position of the sealing lips on the outer face of the liner depend on the individual circumstances of the amputation stump and on the anticipated movement profiles and other individual characteristics and requirements of the person wearing the liner.

By means of a liner as described here, the space between the liner and the prosthesis socket can be evacuated, and the vacuum or the underpressure obtained therein can be maintained. If the prosthesis socket is to be taken off, i.e. the amputation stump with the liner located over it is to be removed from the prosthesis socket, the volume between the inner face of the prosthesis socket and the liner has to be ventilated. For this purpose, a valve is usually present in the prosthesis socket and can be actuated such that the space is ventilated and the wearer is easily able to withdraw the stump from the prosthesis socket.

In a preferred embodiment of a liner according to the present invention, the one-way valve located in the liner is switchable. This means that it can be brought to a first state and to a second state. In the first state, it acts as the already described one-way valve and, in the second state, it can be used as a two-way valve. This means that, in this state, air from the outside can also pass into the space between the prosthesis socket and the liner, such that the space is ventilated and the wearer is able to withdraw the stump from the prosthesis socket. In this way, valves no longer have to be present in the prosthesis socket itself, which greatly simplifies production and reduces the manufacturing costs.

BRIEF DESCRIPTION OF THE DRAWINGS

An illustrative embodiment of the present invention is explained in more detail with reference to the following drawings, in which.

DETAILED DESCRIPTION

Figure 1:
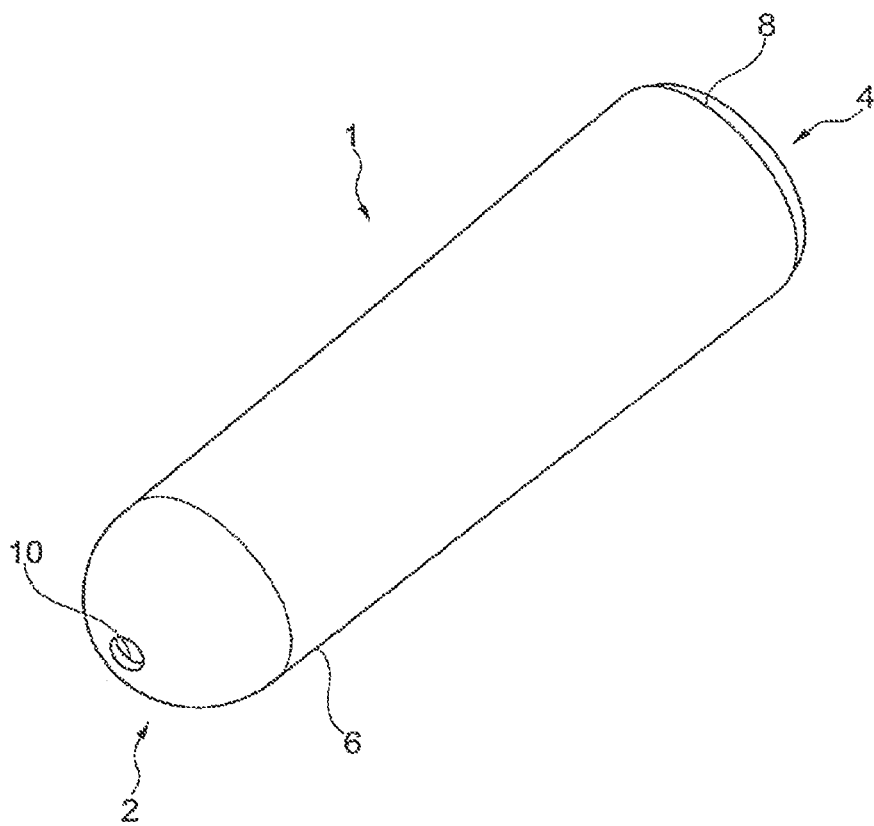
FIG. 1 shows a liner according to a first illustrative embodiment of the present invention.

FIG. 1 shows a liner 1 with a closed distal end 2 and an open proximal end 4. The liner 1 has an outer liner and, arranged therein, an inner liner 8. At the distal end 2 of the outer liner 6, an inlet opening 10 is shown through which air can flow into a pump chamber (not shown in FIG. 1) or a flow channel arranged between the inner liner 8 and the outer liner 6.

Figure 2:
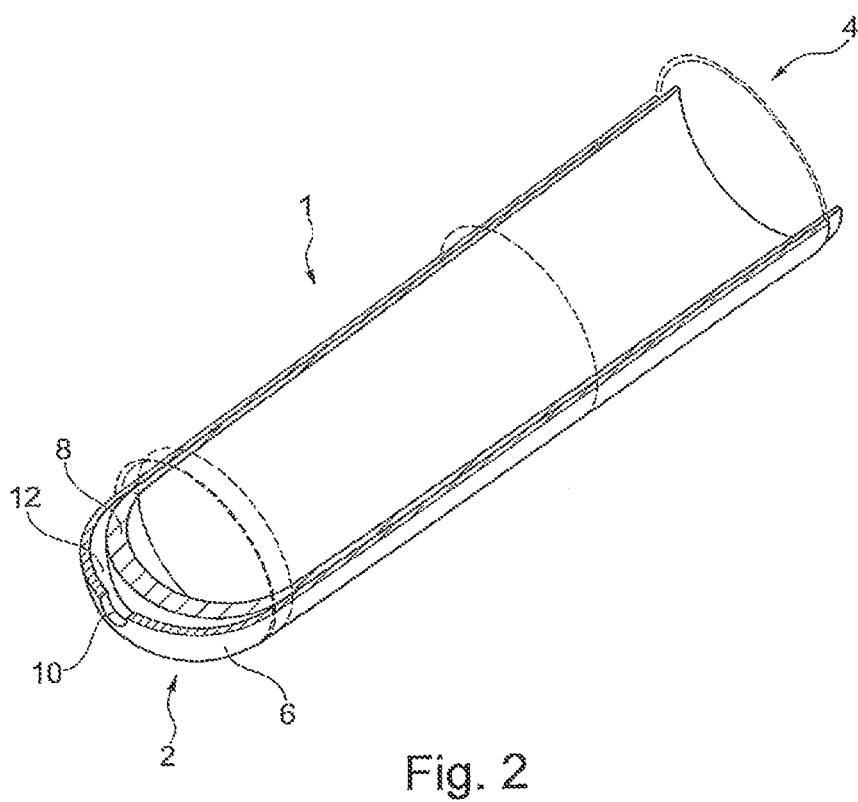
FIG. 2 shows the liner from FIG. 1 in a sectional view.

FIG. 2 shows the liner 1 from FIG. 1 in a sectional view. In the area of the distal end 2, a pump chamber 12 can be seen between the inner liner 8 and the outer liner 6, which pump chamber 12 is connected by the inlet opening 10 to the exterior surrounding the liner 1.

Extending between the inner liner 8 and the outer liner 6 is a flow channel (not shown in FIG. 2), which is connected to the pump chamber 12 via an outlet opening and extends from the pump chamber 12 in the direction of the proximal end 4 of the liner 1. For example, during standing, the pump chamber 12 in a liner 1 shown in FIG. 2 is compressed, since the forces acting during standing press the pump chamber 12 together. The inlet opening 10 then lies on an inner wall of the prosthesis socket (not shown) and is closed by the latter. If this cannot be ensured or cannot be adequately ensured, it is expedient to provide, at the inlet opening 10, a one-way valve that prevents air from flowing out through the inlet opening 10. In this case, the air flows through the outlet opening (not shown) and the flow channel and thus leaves the pump chamber 12.

In a liner 1 according to another illustrative embodiment of the invention, there is no pump chamber arranged between the inner liner 8 and the outer liner 6. Instead, the inlet opening 10 is an opening of the flow channel (not shown in FIG. 2). In this case, the pump chamber is located between the liner and the prosthesis socket but is evacuated in the same manner.

In the swing phase, in which the external force acting on the pump chamber 12 is no longer present, the pump chamber 12 expands, for example on account of restoring forces of an elastic material that is arranged in the pump chamber 12. In this way, air is sucked through the inlet opening 10 into the pump chamber 12, and the volume enclosed between the liner 1 and the surrounding prosthesis socket is evacuated.

Figure 3:
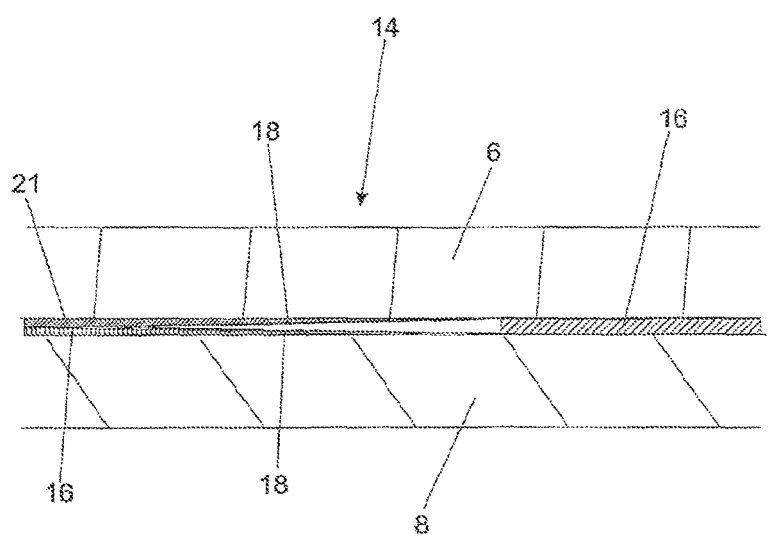
FIG. 3 shows the schematic sectional view through a one-way valve for a liner according to a further illustrative embodiment of the present invention.

FIG. 3 shows a sectional view through a one-way valve 14 which, in the present case, is designed as a flutter valve. Arranged between the inner liner 8 and the outer liner 6 is a flow channel 16 which, for example, can be designed in the form of a tube adhesively bonded between the two liner layers. In the illustrative embodiment shown in FIG. 3, however, the flow channel 16 is made of an air-permeable material.

On the left in FIG. 3, this flow channel 16 is adjoined by the actual one-way valve 14 which, in the present example, has a valve beak composed of two film elements 18. These are, for example, connected via an adhesive layer to the inner liner 8 or the outer liner 6. To the left, the one-way valve 14 is adjoined by a further part of the flow channel 16 which, in the illustrative embodiment shown, is designed as a porous air-permeable material 21.

When an overpressure is built up in the pump chamber 12, for example during walking, the air pressure on the right-hand side of the one-way valve 14 shown in FIG. 3 is greater than on the left-hand side, such that air is forced through the one-way valve 14 and opens the two film elements 18. Air is in this way able to flow out through the one-way valve 14. Thereafter, the external pressure closes the two film elements 18, and the one-way valve 14 is closed such that no air can enter the pump chamber 12 from outside.

Figure 4:
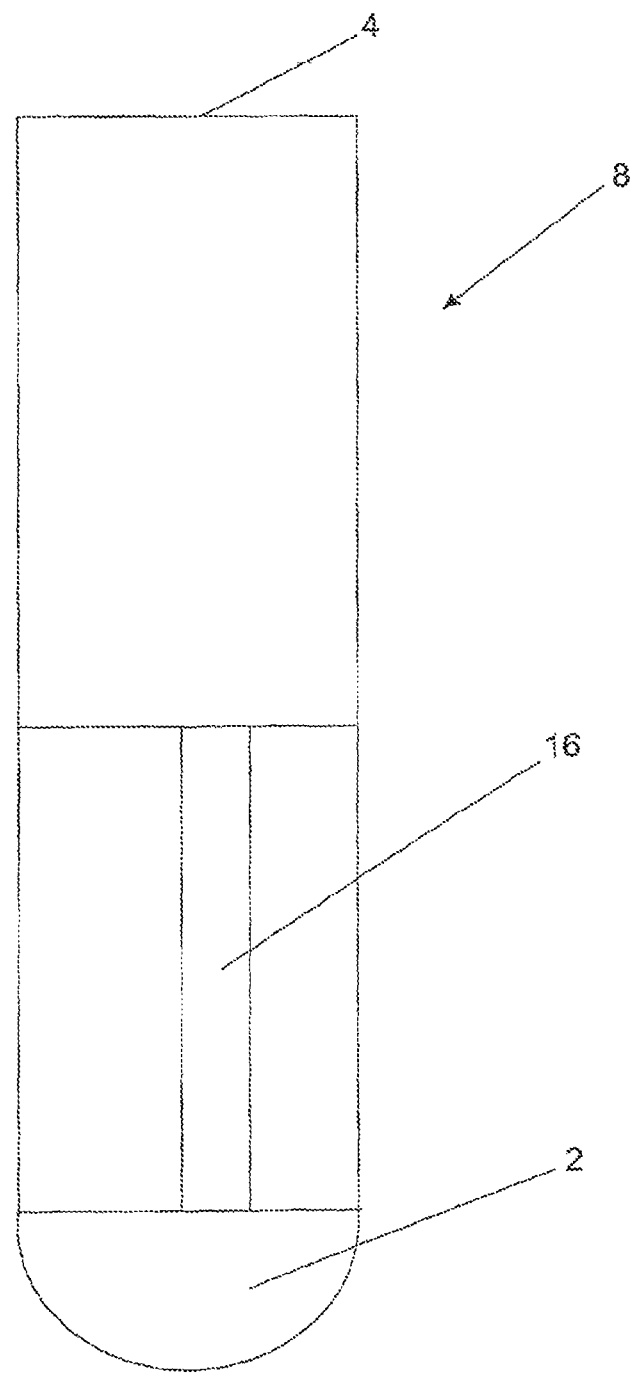
FIG. 4 shows the schematic view of an inner liner for a liner according to a further illustrative embodiment of the present invention.

FIG. 4 shows the inner liner 8 in a schematic view. On the outer face of the inner liner 8 is the flow channel 16 in which, among other things, the one-way valve 14 is also later located. The outlet channel 16 extends as far as the distal end 2 and ends in the central area in the direction of the proximal end 4. In principle, it is not necessary to use a full-surface outer liner 6. It suffices if an outer liner 6 is used that covers the area of the flow channel 16.

Figure 5:
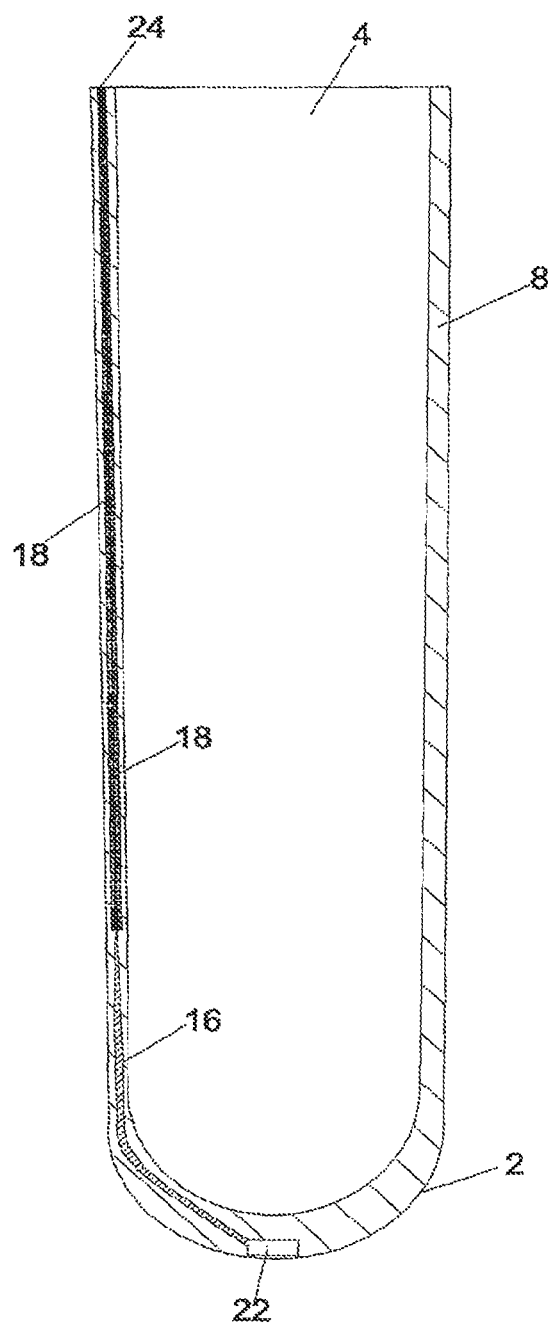
FIG. 5 shows the schematic sectional view through a liner according to a further illustrative embodiment of the present invention.

FIG. 5 shows another embodiment of the inner liner 8, in which an inlet opening 22 is located in the distal end 2. However, the inner liner 8 shown in FIG. 5 can also be inserted, for example, into an outer liner 6 or into a prosthesis socket, such that the inlet opening forms a connection to the intermediate volume located between the inner liner and the respective other component, i.e. the outer liner or the prosthesis socket, wherein the intermediate volume functions as a pump chamber. The inlet opening 22 is connected to the flow channel 16, which is routed in the interior of the inner liner 8 in the direction of the proximal end 4 of the inner liner 8. Above the flow channel 16, the figure shows two film elements 18 which are connected to the flow channel 16 in their lower area and bear on each other in their upper area. If air is now pumped from the inlet opening 22 through the flow channel 16, the two film elements 18 are forced apart from each other and free an upward path for the air, i.e. in the direction of the proximal end 4 of the inner liner 8. At the proximal edge of the outer liner there is an outlet opening 24 through which the air can escape. Since the two film elements 18 in the illustrative embodiment shown bear on each other over a large surface area, no air can pass through the outlet opening 24 into the system, and therefore the inlet opening 22 and the volume optionally adjoining it cannot be ventilated.

Figure 6:
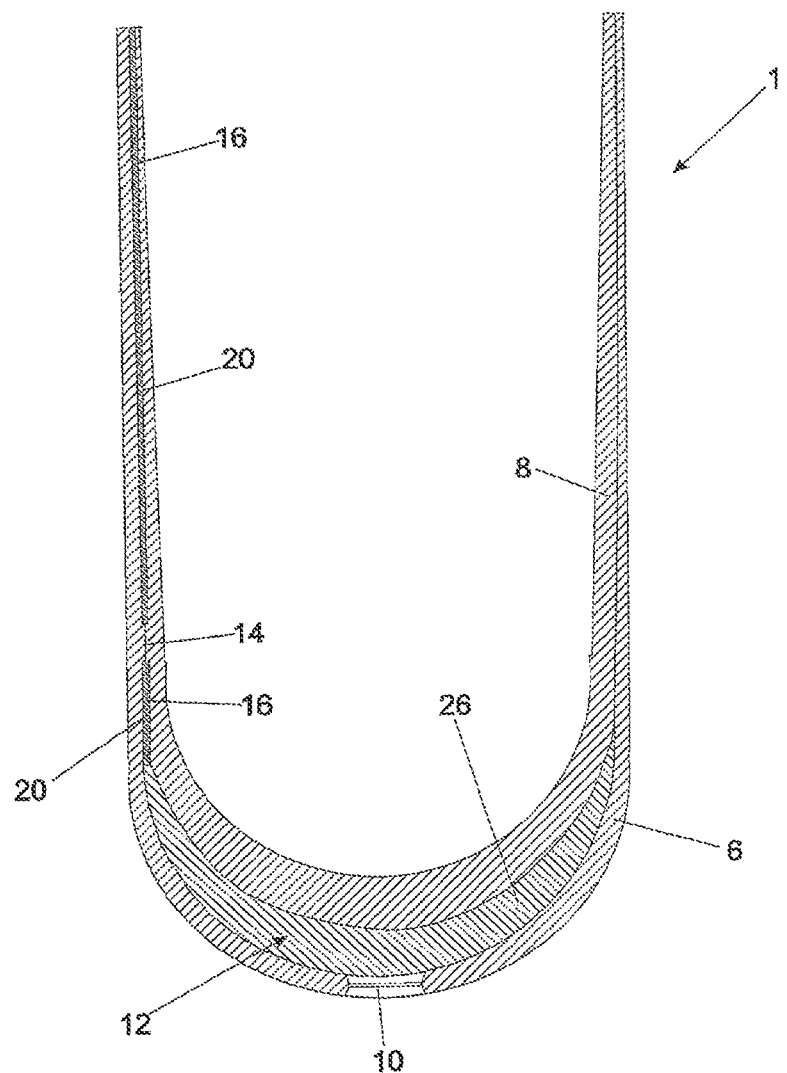
FIG. 6 shows the detail of a further liner in a sectional view.

FIG. 6 shows another embodiment of the liner 1. The inner liner 8 and the outer liner 6, in which the inlet opening 10 is located, can be seen. Between the inner liner 8 and the outer liner 6 is the pump chamber 12, which is filled with a foam material 26. The elasticity of the latter ensures that the pump chamber 12 returns to its original shape after it has been compressed by an external pressure and after the external pressure has been removed. It is thereby ensured that air can once again pass through the inlet opening 10 into the pump chamber 12.

In FIG. 6, the flow channel 16 extends upward from the left-hand end of the pump chamber 12, within the interior between the inner liner 8 and the outer liner 6. It is in the form of a tube 20, for example, and is interrupted by a one-way valve 14 which, in the illustrative embodiment shown, is very short. Whereas the two film elements 18 in the illustrative embodiment shown in FIG. 5 together form the one-way valve 14, which extends along almost the entire length of the liner 1, the one-way valve 14 in the illustrative embodiment shown in FIG. 6 is very short. Nonetheless, it ensures that air can only flow out of the pump chamber 12 through the flow channel 16, whereas an inward flow of air through the flow channel 16 is prevented.

Figure 7:
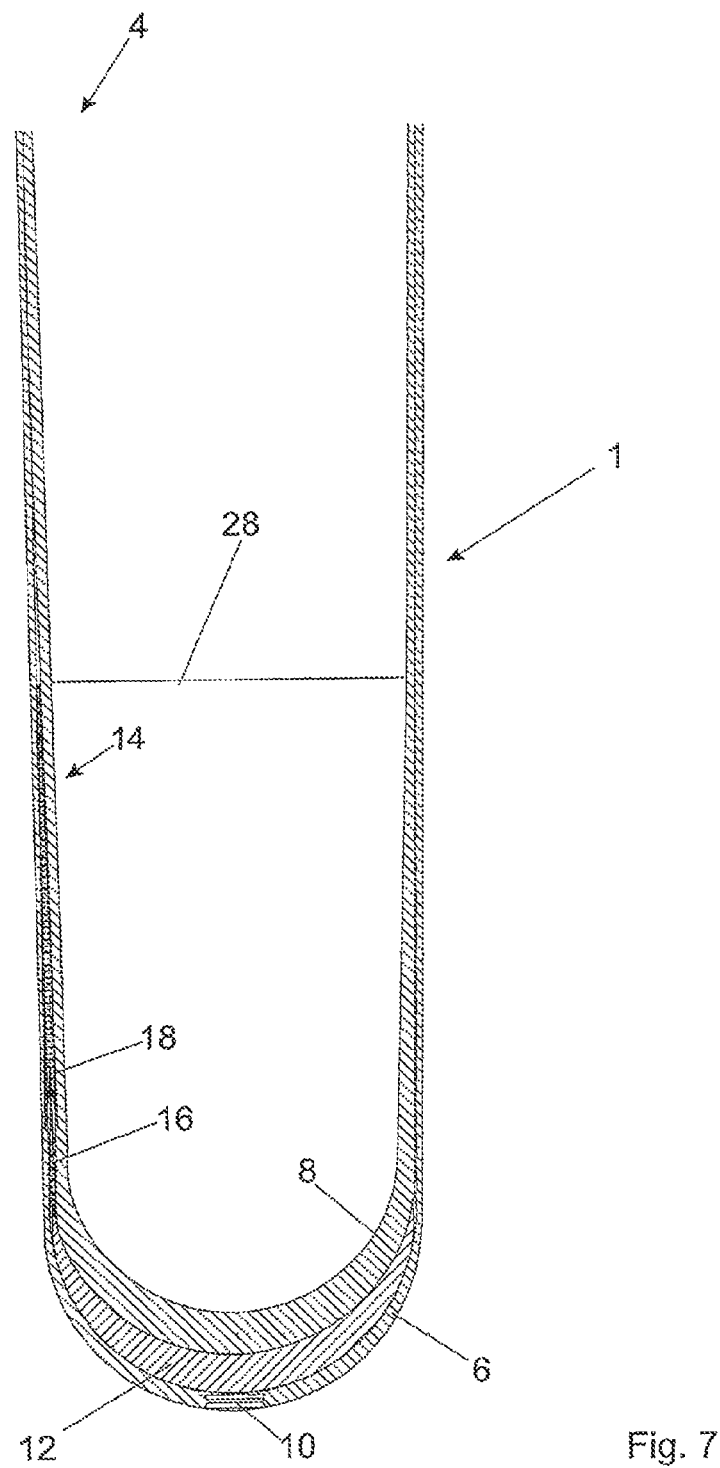
FIG. 7 shows a further liner in a schematic sectional view.

FIG. 7 also shows the liner 1 with the inner liner 8 and the outer liner 6, between which the pump chamber 12 with the inlet opening 10 is located. The flow channel 16 is located in the left-hand area and is surrounded, in the upper area, by two film elements 18 which bear on each other in the further course of the flow channel 16 and together form the one-way valve 14.

However, in contrast to the illustrative embodiment shown in FIG. 5, the flow channel 16 with the two film elements 18 does not extend as far as the proximal end 4 of the liner 1. Instead, the flow channel 16 ends at about half the height of the liner 1. When the liner 1 shown in FIG. 7 is now fitted in place, the outer liner 6 can be turned back at the level of a turn-back edge 28 and thus surrounds a prosthesis socket arranged outside the outer liner 6. This ensures, on the one hand, that there is an airtight seal between the outer liner 6 and the prosthesis socket (not shown in FIG. 7), such that an intermediate volume between the outer liner 6 and the prosthesis socket can be evacuated through the pump chamber 12 without more air being able to flow in.

On the other hand, the turning back of the outer liner 6 has the effect that air which is forced through the pump chamber and the flow channel 16 by the film elements 18 can now leave the liner 1 at the level of the turn-back edge 28. The turn-back edge 28, in particular its position along the liner 1, is depicted only schematically and not true to scale.

Figure 8:
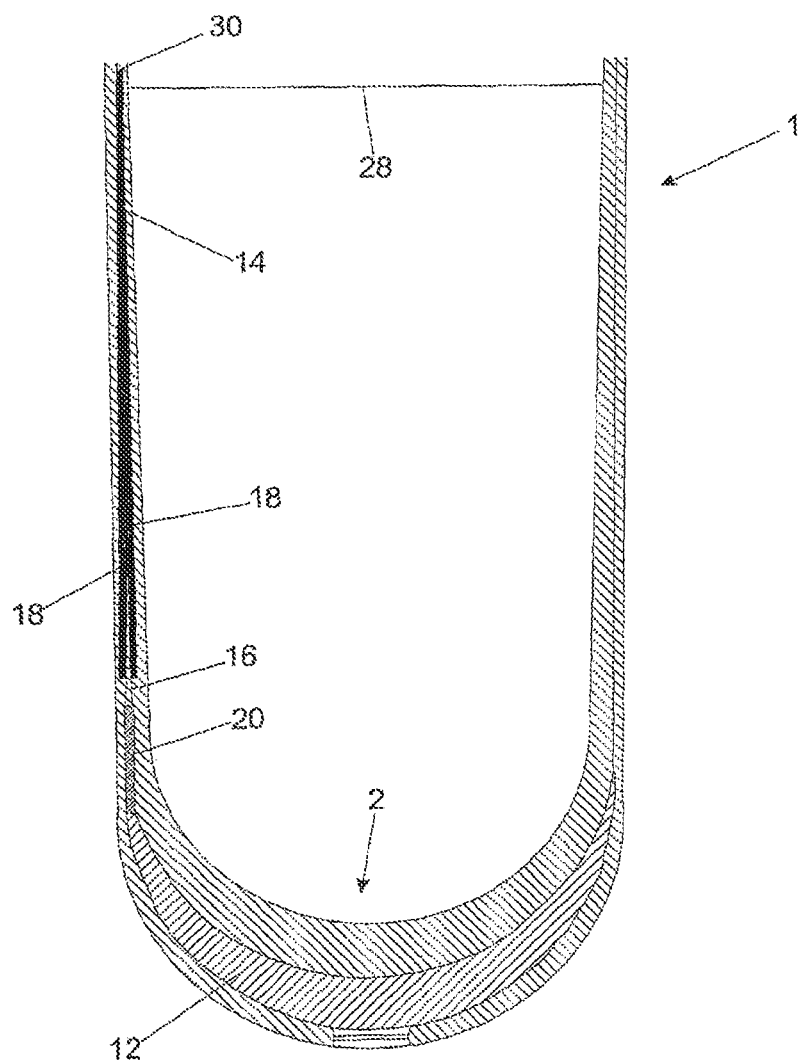
FIG. 8 shows an enlarged detail from FIG. 7.

FIG. 8 shows an enlarged detail from FIG. 7. This shows the flow channel 16, which is formed by a tube 20 in the lower area, i.e. toward the distal end 2. It is adjoined by the two film elements 18, which bear on each other in the direction of the proximal end 4 of the liner 1 and thus together form the one-way valve 14. The inner liner 8 and the outer liner 6 are advantageously secured on each other over their complete surface area, in order to ensure an optimal hold of the two liners on each other. However, in the illustrative embodiment shown, this applies only in the distal area as far as the turn-back edge 28. Above the turn-back edge 28, which may only be an imaginary line, the two liners 6, 8 can be moved relative to each other. In particular, the outer liner 6 can be turned back and thus ensures a seal between the outer liner 6 and the prosthesis socket (not shown). In this case, a proximal channel end 30 is located at the upper edge of the liner, such that air can flow out of the pump chamber 12. As an alternative or addition to this solution, it is also possible, in liners 1 according to the illustrative embodiments shown in FIGS. 7 and 8, that air forced through the flow channel 16 and the two film elements 18 by the one-way valve 14 can leave the liner 1 laterally at the proximal channel end 30 and, if appropriate, can be carried away via a passage through the prosthesis socket.

Figure 9:
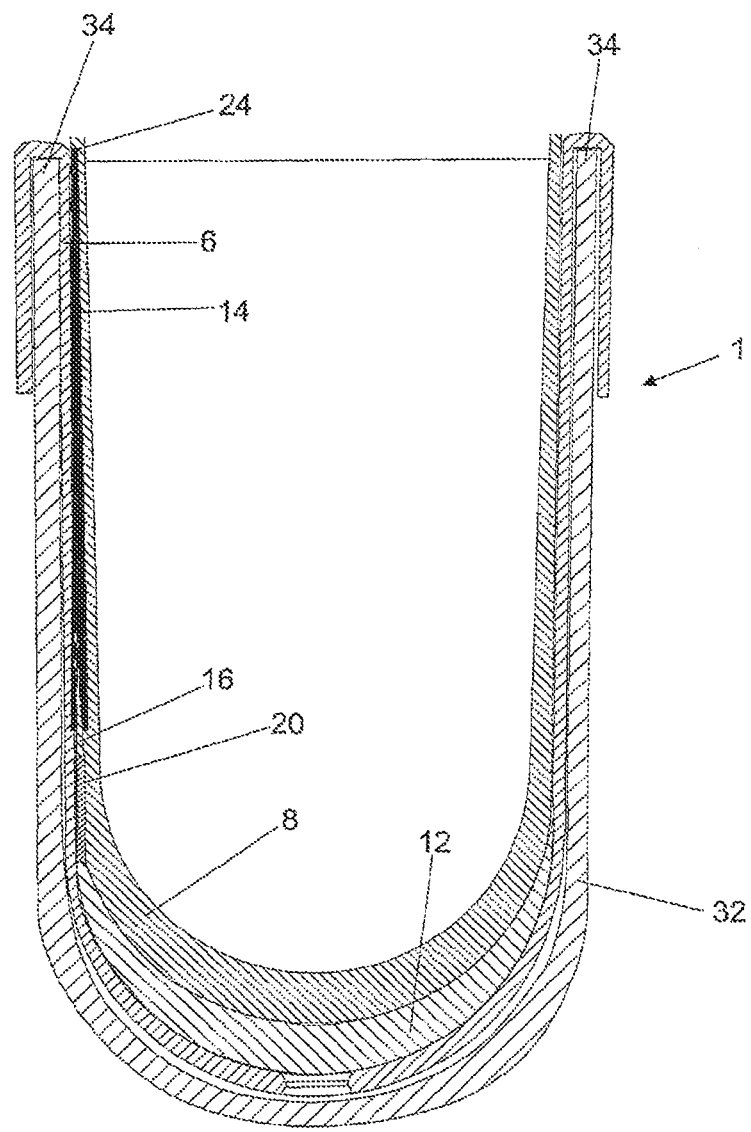
FIG. 9 shows a further liner in a schematic sectional view.

FIG. 9 shows a further sectional view through the liner 1 with inner liner 8 and outer liner 6 and, arranged between them, pump chamber 12, the tube 20, the flow channel 16 and the one-way valve 14. The liner 1 corresponds to the liners shown in FIGS. 7 and 8, but in FIG. 9 it is shown arranged in a prosthesis socket 32. It will be seen that the outer liner 6 is turned back across a proximal edge 34 of the prosthesis socket 32. On the one hand, the stability is thereby increased, and, on the other hand, the outlet opening 24 is freed.

Figure 10:
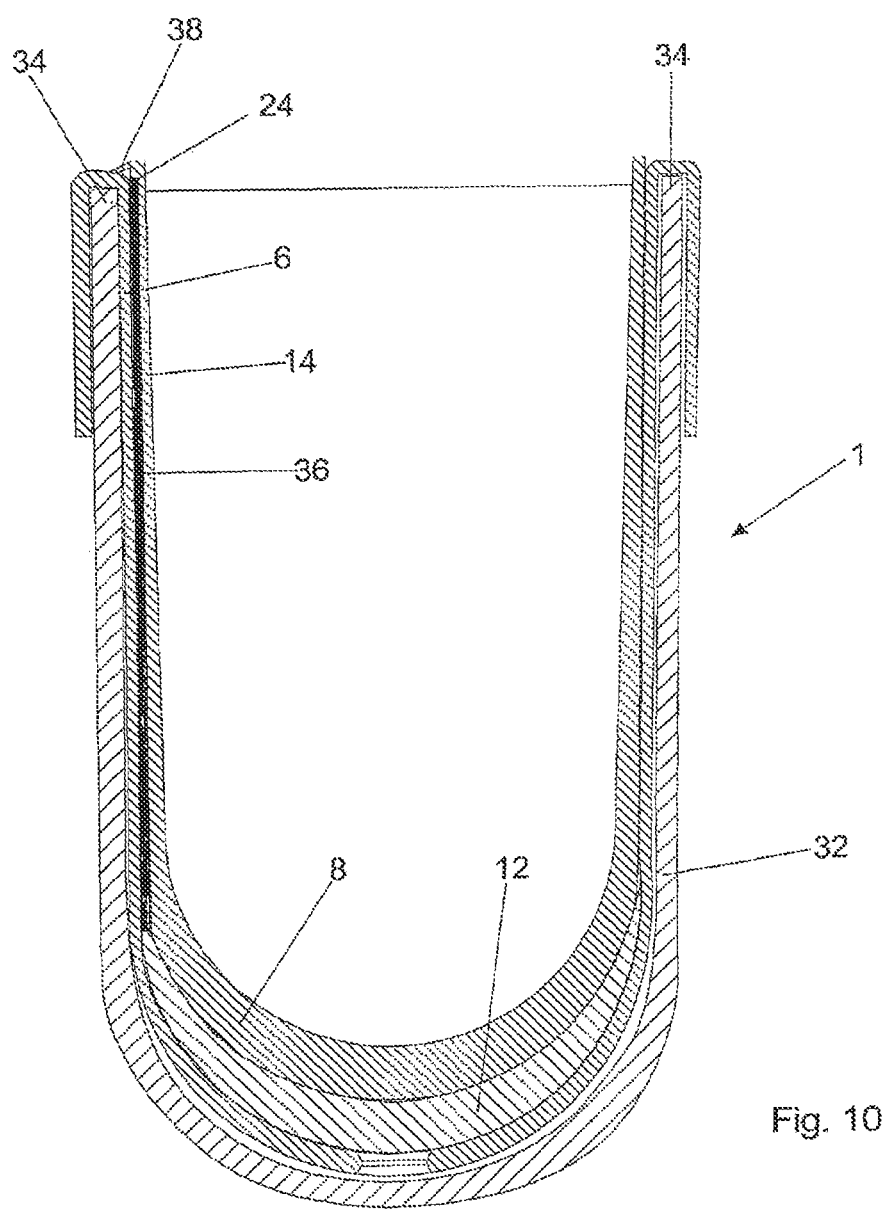
FIG. 10 shows a further liner in a schematic sectional view.

FIG. 10 shows a further liner 1 in a sectional view which strongly resembles the liner 1 shown in FIG. 9. It too comprises the outer liner 6, the inner liner 8 and the pump chamber 12 and, in the illustrative embodiment shown, is inserted into the prosthesis socket 32. The outer liner 6 is turned back over the proximal edge 34. However, in the illustrative embodiment shown, the valve 14 is formed by an additional liner layer 36, which is permeable to air. In the loaded state, the pump chamber 12 is compressed, such that air can be conveyed upward from the pump chamber 12 through the liner layer 36 in the illustrative embodiment shown. The outlet opening 24 is covered here by a closure element 38 which is arranged on the inner liner 8 and which is so flexible and elastic that it can be opened by the air flowing through the valve 14.

In the unloaded state of the prosthesis, the pump chamber 12 expands, such that an underpressure forms therein. On the one hand, inward flow of air is prevented by the compression of the liner layer 36 caused by the ambient pressure or by the pressure exerted by the prosthesis socket 32, and, on the other hand, by the closure element 38 which closes the outlet opening 24.

Figure 11:
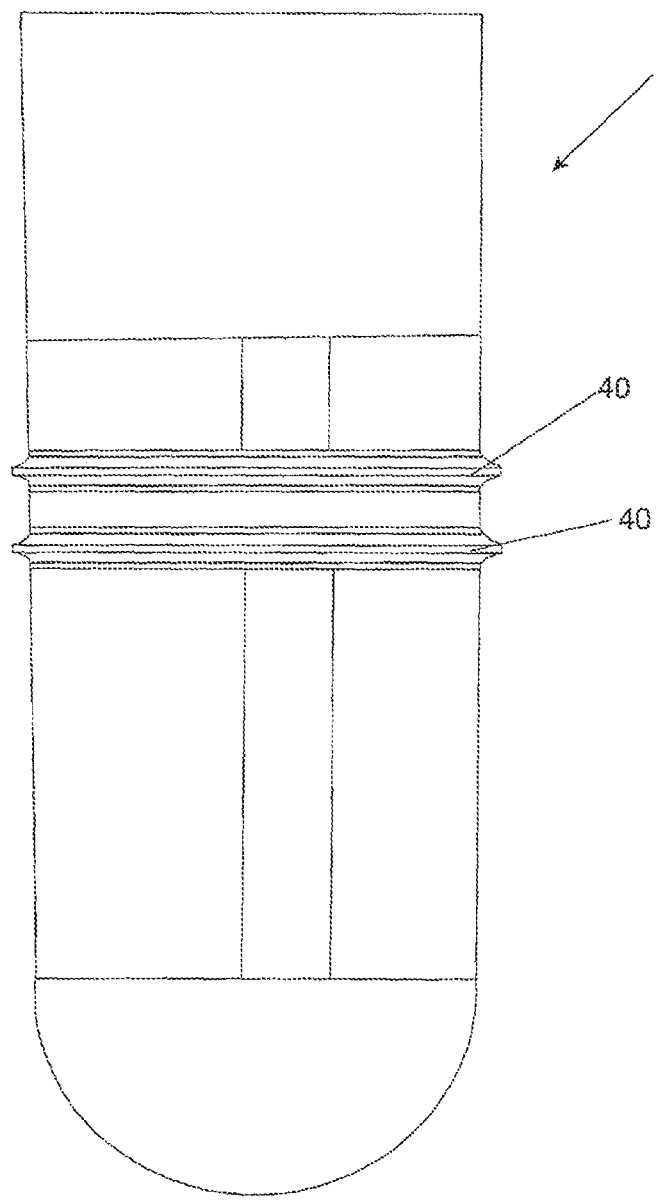
FIGS. 11 to 14 show further liners in schematic sectional views.

The liner 1 shown in FIG. 11 corresponds to the liner shown in FIG. 4, with two sealing lips 40 now arranged around the liner 1 in FIG. 11. These sealing lips 40 ensure leaktight contact with the inner face of a prosthesis socket pulled on over the liner 1.

Figure 12:
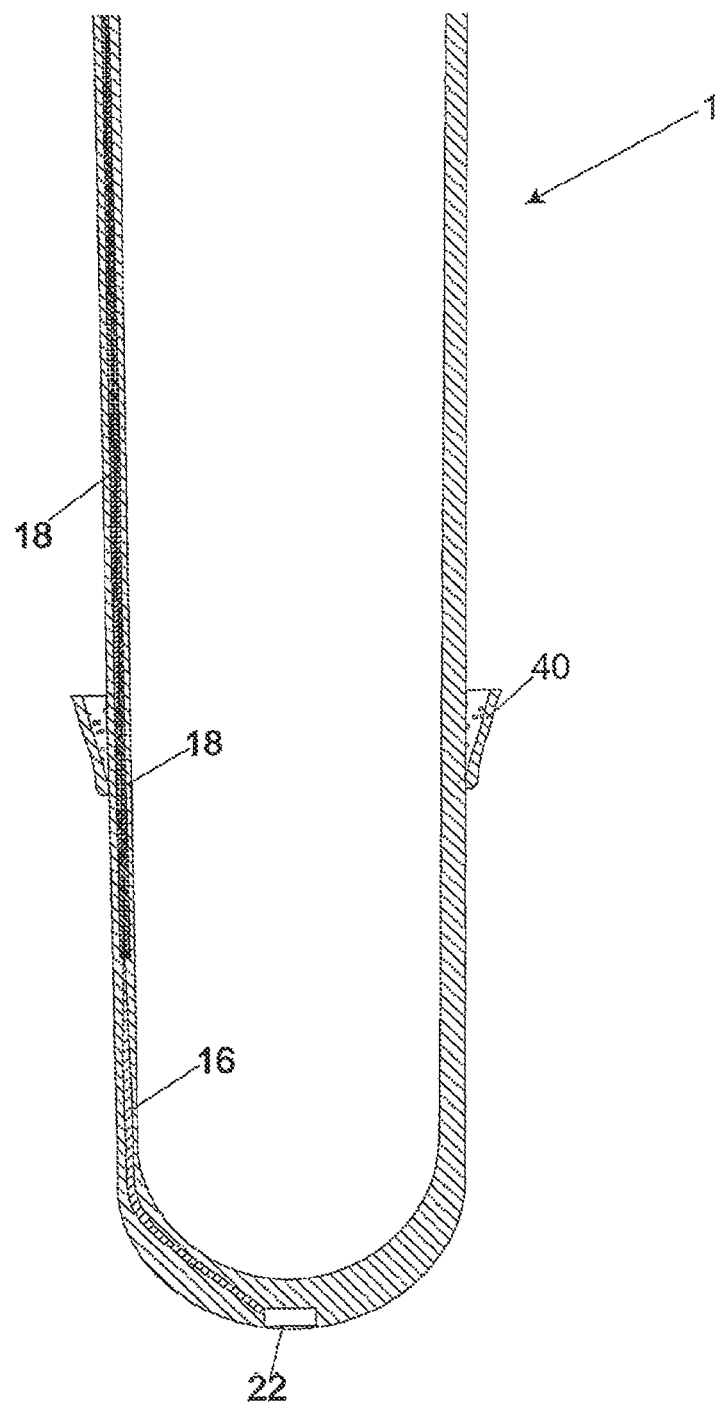

The liner 1 shown in FIG. 12 corresponds to the liner shown in FIG. 5, which liner, via the inlet opening 22 and the flow channel 16, is able to pump air from the space between the liner 1 and a prosthesis socket pulled on over the latter. The two film elements 18 are present for this purpose. This liner 1 now also has a sealing lip 40, which is arranged protruding from the outer face of the liner. In the illustrative embodiment shown, it has been produced as a separate component and, for example, has been adhesively bonded to the liner 1. Alternatively, however, it could also be produced in one-piece with the liner 1. The sealing lip ensures a leaktight contact with the prosthesis socket that is pulled on over the liner 1.

Figure 13:
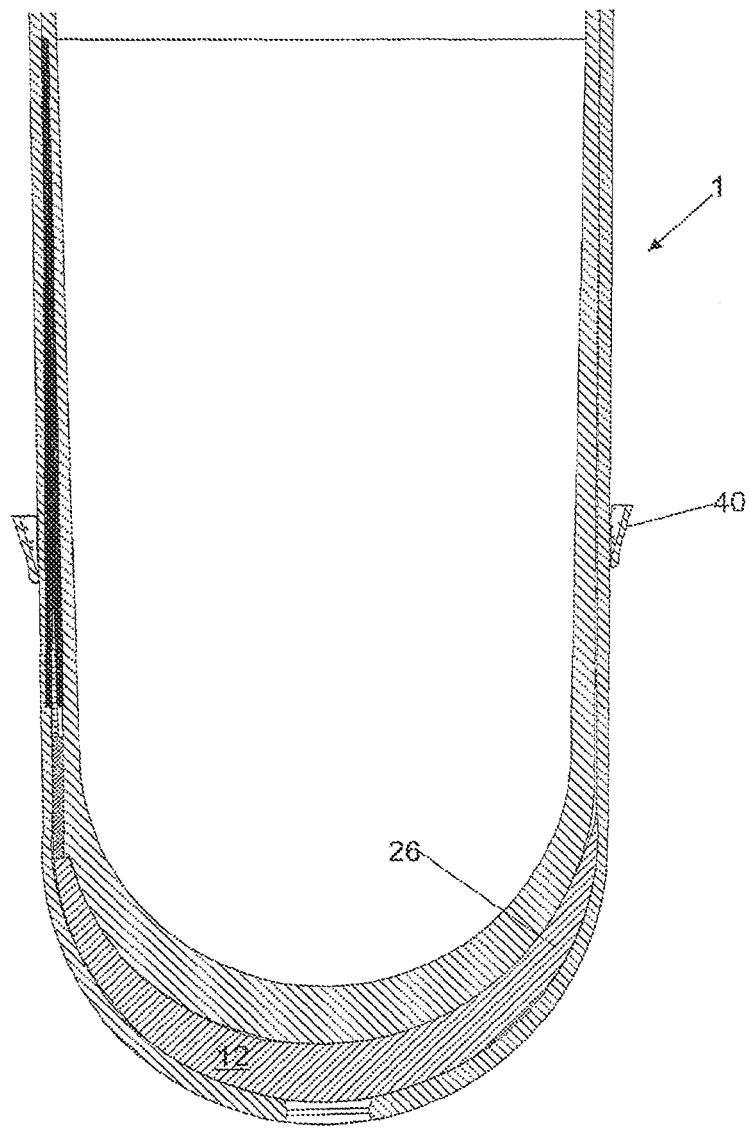

The liner 1 shown in FIG. 13 corresponds to the liner shown in FIG. 6 and has a pump chamber 12 made of the foam material 26. Here too, a sealing lip 40 is arranged on the outer face of the liner.

Figure 14:
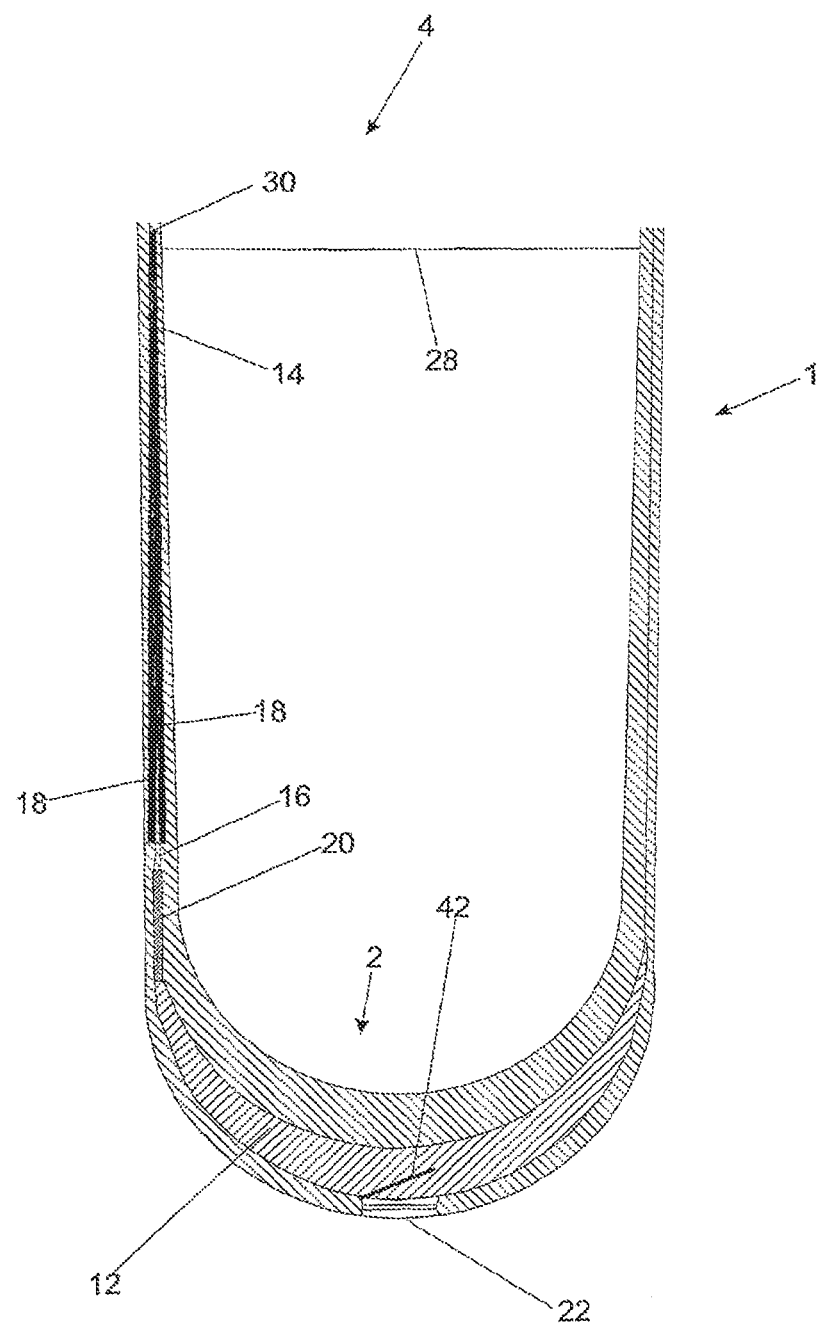

The liner 1 shown in FIG. 14 corresponds to the liner from FIG. 8. However, the liner 1 shown in FIG. 14 additionally has a second one-way valve 42, which is arranged on the inner face of the inlet opening 22. For example, this one-way valve can be in the form of an individual film element, which is arranged as shown in FIG. 14. In the stance phase, when the amputation stump presses the liner 1 into the prosthesis socket 32, the second one-way valve 42 completely closes the inlet opening 22. In this case, air located in the pump chamber 12 is expelled through the one-way valve 14 and the flow channel 16. In the swing phase, the prosthesis socket is unloaded and the second one-way valve 42 is brought to the position shown in FIG. 14, such that air can pass through the inlet opening 22 into the pump chamber 12.

The invention claimed is:
1. A liner for a prosthesis, comprising:
   an inner face;
   an outer face;
   at least one flow channel having at least one inlet opening and at least one outlet opening, the at least one flow channel extending between the inner face and the outer face;
   a one-way valve arranged in the at least one flow channel in such a manner that a medium can flow through the one-way valve only from the at least one inlet opening to the at least one outlet opening, the one-way valve being configured to evacuate a volume between a distal end of the liner and a prosthesis socket of the prosthesis.
2. The liner according to claim 1, wherein the liner has an inner liner and an outer liner at least in sections of the liner.
3. The liner according to claim 2, wherein at least one of the inner liner and the outer liner is made of polyurethane or silicone.
4. The liner according to claim 2, wherein the one-way valve is formed from the inner liner and the outer liner.
5. The liner according to claim 2, wherein the at least one inlet opening is a hole formed in the outer liner.
6. The liner according to claim 2, wherein the inner liner and the outer liner are arranged positioned on each other in a proximal area of the liner in such a manner that the outer liner can be turned back separately from the inner liner.
7. The liner according to claim 1, wherein the one-way valve is designed as a flutter valve.
8. The liner according to claim 7, wherein a valve beak of the flutter valve comprises two film elements.
9. A liner for a prosthesis, comprising:
   an inner face;
   an outer face;
   at least one flow channel having at least one inlet opening and at least one outlet opening, the at least one flow channel extending between the inner face and the outer face;
   a one-way valve arranged in the at least one flow channel in such a manner that a medium can flow through the one-way valve in a direction only from the at least one inlet opening to the at least one outlet opening;
   at least one pump chamber positioned between the inner face and the outer face and fluidically connected to the at least one flow channel.
10. The liner according to claim 9, wherein the liner has an inner liner and an outer liner at least in sections of the liner.
11. The liner according to claim 10, wherein at least one of the inner liner and the outer liner is made of polyurethane or silicone.
12. The liner according to claim 10, wherein the one-way valve is formed from the inner liner and the outer liner.
13. The liner according to claim 10, wherein the at least one inlet opening is a hole formed in the outer liner.
14. The liner according to claim 10, wherein the inner liner and the outer liner are arranged positioned on each other in a proximal area of the liner in such a manner that the outer liner can be turned back separately from the inner liner.
15. The liner according to claim 9, wherein the one-way valve is designed as a flutter valve.
16. The liner according to claim 15, wherein a valve beak of the flutter valve comprises two film elements.
17. The liner according to claim 9, wherein the at least one pump chamber has a peripheral wall made of an elastically deformable material.
18. The liner according to claim 17, wherein the peripheral wall is formed from the inner liner and the outer liner.

19. The liner according to claim 17, wherein the elastically deformable material comprises an open-pore material and is located in the pump chamber.

20. The liner according to claim 9, wherein at least one of the inlet opening is located distally on the liner and the outlet opening is located proximally on the liner.

* * * * *

UNITED STATES PATENT AND TRADEMARK OFFICE
CERTIFICATE OF CORRECTION

PATENT NO. : 10,335,295 B2  
APPLICATION NO. : 15/323618  
DATED : July 2, 2019  
INVENTOR(S) : Muller et al.

Page 1 of 1

It is certified that error appears in the above-identified patent and that said Letters Patent is hereby corrected as shown below:

On the Title Page

Item (54) and in the Specification, Column 1, Lines 1-5, the title should read as follows:  
LINER FOR A PROSTHESIS Signed and Sealed this  
Thirteenth Day of August, 2019

Andrei Iancu  
*Director of the United States Patent and Trademark Office*